United States Patent
Krbechek

[11] Patent Number: 5,808,130
[45] Date of Patent: Sep. 15, 1998

[54] ESTERIFICATION OF PHENOLS

[75] Inventor: Leroy Krbechek, Santa Rosa, Calif.

[73] Assignee: Henkel Corporation, Plymouth Meeting, Pa.

[21] Appl. No.: 714,279

[22] Filed: Sep. 17, 1996

Related U.S. Application Data

[63] Continuation-in-part of Ser. No. 671,361, Jun. 27, 1996, abandoned.

[51] Int. Cl.$^6$ ..................................................... C07C 69/00
[52] U.S. Cl. ................................................................. 560/130
[58] Field of Search ............................................ 560/130

[56] References Cited

U.S. PATENT DOCUMENTS

| | | |
|---|---|---|
| 2,212,509 | 8/1940 | Cherry . |
| 2,807,639 | 9/1957 | Rickert . |
| 4,374,263 | 2/1983 | Hancock et al. . |
| 5,300,689 | 4/1994 | Krbechek ................................. 564/259 |
| 5,349,088 | 9/1994 | Krbechek ................................. 564/259 |
| 5,488,161 | 1/1996 | Krbechek ................................. 564/259 |

FOREIGN PATENT DOCUMENTS 63-277645  6/1973  Japan .

OTHER PUBLICATIONS

*Synthetic Organic Chemistry,* Wagner and Zook, 1953, p. 480.

M.B. Hocking, *J. Chem. Ed.,* vol. 59, p. 527 (1980).

*Primary Examiner*—Paul J. Killos
*Attorney, Agent, or Firm*—Ernest G. Szoke; Wayne C. Jaeschke; Frank E. Robbins

[57] ABSTRACT

Relates to the direct esterification of phenols, particularly alkyl-substituted phenols, with a carboxylic acid or anhydride, in the presence of a strong acid catalyst. Also relates to the use of the acid anhydride to drive the esterification reaction to completion, where an initial reaction mixture has been formed using the carboxylic acid. Further relates to the achievement of economies in esterification by recovering dilute aqueous acid when either the acid or anhydride is used initially, for recycling to achieve economies of acid use.

63 Claims, 1 Drawing Sheet

ESTERIFICATION OF PHENOLS

RELATED APPLICATIONS

This application is a continuation-in-part of an earlier application, Ser. No. 08/671,361, filed Jun. 27, 1996, abandoned, attorney docket M 5636 MIN (33663).

FIELD OF THE INVENTION

This invention relates to practical processes for the direct esterification of phenols. It is particularly applicable to alkyl-substituted phenols, and especially to phenols that are substituted with branched chain alkyl.

BACKGROUND OF THE INVENTION

Direct esterification of alkanols is effected by refluxing a carboxylic acid and an alcohol such as an alkanol with a small amount of an acid catalyst, such sulfuric acid. The equilibrium of the reaction can be shifted to favor ester formation by utilizing an excess of one of the reactants, and/or by the removal of the water that is formed during the reaction.

There are widespread indications in the chemical literature that phenols do not undergo direct esterification to an appreciable extent. Thus, the possibility of direct esterification has often been dismissed as not being feasible. Methods of using acid derivatives, for esterification, have been developed for the purpose of esterifying phenols.

Many of the alkylphenol esters are valuable for their own properties, and in addition, as intermediates for the production of other compounds. For the production of an acetate of an alkylphenol, attempts have been made to esterify the alkylphenol by direct reaction with acetic acid. Unfortunately, direct esterification with acetic acid within a short period of time and in good yields has been an elusive goal.

Direct esterification by acetylation of an alkylphenol, where practiced at all, generally makes use of acetic anhydride. This is expensive. In addition, it is difficult to drive the reaction to completion, so that a substantial amount of the acetic anhydride used is not consumed in the esterification, and must be recovered as dilute acetic acid.

Direct esterification with acetic acid requires a great many hours for the reaction to go to a reasonable degree of completion. Better results are obtained with acetic anhydride.

An example of the use of an acetate ester of an alkylphenol as an intermediate is in the production of oxime liquid metal extraction reagents. One such use is described in greater detail in U.S. Ser. No. 08/635,865, filed Apr. 23, 1996, which is incorporated herein by reference. That application describes the production of 5-alkylsalicylaldoximes, wherein the 2-acetate is a key intermediate in the production of a 5-alkylsalicylaldehyde. One important use of alkylphenol acetates would be in the Fries rearrangement. This reaction can be carried out to rearrange 4-isononylphenyl acetate to yield 2-hydroxy-5-isononylacetophenone, which can be purified and oximated, with the oxime being useful as a metal extractant.

In the well known liquid extraction process, the metal extractant is dissolved in a solvent, and is contacted with an aqueous metal solution to form a complex with the metal, which complex is soluble in an organic solvent. The organic phase is then separated from the aqueous phase, and the metal content is stripped from the organic phase, usually by means of an acid.

The extractants that are made from the intermediates that can be produced by the esterification processes of the present invention are characterized as having sufficient solubility in one or more solvents or mixtures thereof to make about a 2% solution, and they are essentially insoluble or immiscible with water. At the same time, each should form a complex with a metal, such as copper, which complex, likewise, is soluble in the organic solvent to at least the extent of about 2% by weight.

These characteristics are generally achieved by having alkyl substituents on the aryl ring of the extractant, that have at least 3 alkyl carbon atoms. Usually it is preferred, although not essential, not to have more than 25 carbon atoms total in the alkyl substituents since these substituents contribute to the molecular weight of the oxime extractant without improving operability. Large substituents, also, increase the amount of oxime needed for a given copper or other metal loading capacity. In general, the branched chain alkyl substituents effect a greater degree of solubility of the reagent and of the copper or other metal complex and, accordingly, these are preferred, especially those of 6 to 18 carbons.

Oxime extractants are often produced by reacting an organic carbonyl compound such as an aldehyde or ketone with hydroxylamine, usually generated from a hydroxylamine salt such as hydroxylammonium sulfate or hydroxylammonium chloride.

Current oximation procedures employ standard oximation processes with an alcohol such as methanol as a solvent, hydroxylammonium sulfate, and sodium acetate. Improved or alternate processes are described in three U.S. Pat. Nos. 5,300,689; 5,349,088, and 5,488,161. The oximes, such as the hydroxy aryl ketoximes and hydroxy aryl aldoximes, which are substantially insoluble in water but soluble in water-immiscible organic solvents, such as kerosene, are useful in solvent extraction processes for the recovery of metals, particularly copper, from aqueous solutions.

Reagents frequently employed in commercial processes for copper recovery are included among those offered by Henkel Corporation under the LIX® trademark, viz., LIX®63, LIX®65N, LIX®64, LIX®64N, LIX®70, LIX®71, LIX®73, LIX®34, LIX®54, LIX®605, LIX®617, LIX®622 and LIX®6022, LIX®860, LIX®984, LIX®973, and LIX®84.

Briefly noted, LIX®63 extractant includes, in addition to a liquid hydrocarbon diluent, an aliphatic α-hydroxy oxime extractant (5,8-diethyl-7-hydroxy-dodecan-6-oxime). The LIX®65N extractant includes an alkyl substituted hydroxy benzophenone oxime (2-hydroxy-5-nonyl benzophenone oxime). The LIX®64 extractant and the LIX®64N extractant incorporate benzophenone oxime extractants (2-hydroxy-5-dodecyl benzophenone oxime and 2-hydroxy-5-nonyl benzophenone oxime, respectively) in combination with an aliphatic α-hydroxy oxime.

Formulation of the LIX®70 extractant involves the combination of a benzophenone oxime extractant containing an electron withdrawing substituent (2-hydroxy-3-chloro-5-nonyl benzophenone oxime) with an aliphatic α-hydroxy oxime. The LIX®71 and LIX®73 formulations both include a mixture of two benzophenone oximes, one of which has an electron withdrawing substituent (i.e., a mixture of 2-hydroxy-5-nonyl benzophenone oxime and 2-hydroxy-3-chloro-5-nonyl benzophenone oxime) with the latter reagent further including an aliphatic a-hydroxy oxime.

The LIX®34 extractant and the LIX®54 extractant incorporate alkaryl sulfonamido quinoline and β-diketone extractants, respectively. The LIX®605 extractant, the LIX®617 extractant, the LIX®622 extractant, and the LIX®6022 extractant, on the other hand, employ alkyl substituted hydroxy benzaldoxime (salicylaldoxime) extractants. Thus, the LIX®605 extractant and the LIX®617 extractant include 2-hydroxy-5-nonyl benzaldoxime extractants with, respectively, nonylphenol and tridecanol additives. The LIX®622 extractant and the LIX®6022 extractant comprise formulations of 2-hydroxy-5-dodecyl benzaldoxime and a tridecanol additive in approximately 4:1 and 1:1 w/w ratios, respectively.

The extractant PT-5050 is offered for sale by ZENECA, Inc. of Phoenix, Ariz. It is believed to be a formulation comprising 2-hydroxy-5-nonyl benzaldoxime and a tridecanol additive in an approximately 2:1 w/w ratio.

There exists a general need in the art for more efficient processes for producing such oxime extractants.

In my copending patent application identified above and incorporated herein by reference, there are described processes for the production of substituted hydroxyarylaldehydes that, after oximation, are useful metal extractants. More specifically, my earlier application relates to precursors that are useful in the synthesis of hydroxyarylaldehydes, such as, for example, 4-isoalkylphenyl allyl ethers; 2-allyl-4-isoalkyl-phenols; and 2-hydroxy-5-isoalkyl-beta-methylstyrenes. That application relates to processes for making each of these and other novel precursors useful in the production of hydroxyarylaldehydes, and particularly, 5-isoalkyl salicylaldehydes. That application also relates to a process comprising the ozonization of solutions of 2-hydroxy-5-alkyl-beta-methylstyrenes, whereby substantial amounts of 5-alkyl-substituted salicylaldehydes are formed, from which the desired metal extractants may be produced by oximation.

That earlier invention uses 4-alkylphenols, preferably 4-isoalkylphenols, as starting materials.

SUMMARY OF THE PRESENT INVENTION

The present invention relates to the esterification of phenol, particularly alkylphenols, and more particularly branched chain alkylphenols, by practical direct esterification processes.

The invention provides reasonable conversions of phenol and of alkylphenols to form their esters by direct esterification with carboxylic acids and anhydrides, preferably, for present purposes, acetic acid or acetic anhydride. The alkyl substitutent or substituents on the phenol may be straight or branched chain, or in the case of plural alkyl substituents, a mixture of these. It is preferred that the total alkyl substitution on the aryl ring not exceed a total of 25 carbons, and that at least one substituent be a branched chain alkyl, para to the hydroxyl position. Most preferably the branched chain alkyl comprises an isononyl or an isododecyl substituent.

Contrary to what one might expect based on experience and the reports in the literature, the best results in direct esterification with a carboxylic acid appear to be achieved at relatively low molar ratios of the alkylphenol to the carboxylic acid, in a relatively short time, in some cases, in 2–4 hours, under reflux, and using a strong acid catalyst.

Moreover, the direct esterification for the production of an acetate ester can be achieved using either aqueous or glacial acetic acid. Acetic anhydride with the same strong acid catalyst can be employed to drive the reaction to substantial completion.

The less expensive aqueous carboxylic acids having up to 6 carbons are preferred for direct esterification from the standpoint of economics, but similar considerations as to reaction conditions apply to the use of other carboxylic acids. Generally, it is more practical to use carboxylic acids at concentrations of 90% or more, preferably of 95% or more, but lower concentrations can be used, with proper equipment and operating conditions, to permit water removal, so as to concentrate the acid. Elevated temperatures are used, preferably reflux temperatures where water is taken off along with carboxylic acid, in an azeotrope with a hydrocarbon solvent. The azeotrope preferably is condensed so that at least some of the carboxylic acid can be recovered as an aqueous form of the carboxylic acid. This acid condensate can then be reused, permitting greater economy in the process.

For practical reuse, the aqueous carboxylic acid condensate may be recovered and transferred either to a new reaction mixture or to an existing reaction mixture, where in either case there is an organic solvent present that forms an azeotrope, for water removal. Under reflux and condensation, water is removed until the concentration of the carboxylid acid is sufficiently high for it to become active in the esterification reaction. After the esterification reaction has proceeded to a reasonable extent, the carboxylic acid anhydride may be added to drive the reaction towards completion.

Esterification can thus be carried out in this two step process, using the carboxylic acid in an initial esterification step, then using the anhydride of the carboxylic acid, both in the presence of a strong acid catalyst, and at an elevated temperature, to carry the reaction to completion. In one preferred embodiment, the carboxylic acid may be acetic acid, and the anhydride may be acetic anhydride. The acetic anhydride may be used with the same strong acid catalysts employed to drive the initial reaction forward.

The invention also embraces a method for producing an ester of a phenol and a carboxylic acid by reacting the phenol with a carboxylic acid anhydride in the presence of a strong acid catalyst. This is also a direct esterification reaction. It can go forward rapidly at a relatively low temperature, such as 70° C., although it proceeds at a more rapid rate at a higher temperature. A slight excess of the acid anhydride is useful. Since the carboxylic acid anhydrides generally are expensive as compared to their acids, there is usually an economic incentive to use the two step process of the invention, where the anhydride is used only in the final stages of the esterification reaction, to drive it toward completion.

For both of these types of direct esterification, the amount of strong acid catalyst that is effective is relatively small. For example, in the case of the production of acetates, the use of a molar amount of 0.001 moles of the strong acid catalyst, for every mole of the phenolic compound being esterified, is adequate.

The direct esterification processes of the invention are expected to go forward with aliphatic carboxylic acid in general, and with aryl carboxylic acids to some extent. The direct esterification reactions with acid anhydrides are believed to be general.

DETAILED DESCRIPTION OF THE INVENTION

Figure 1:
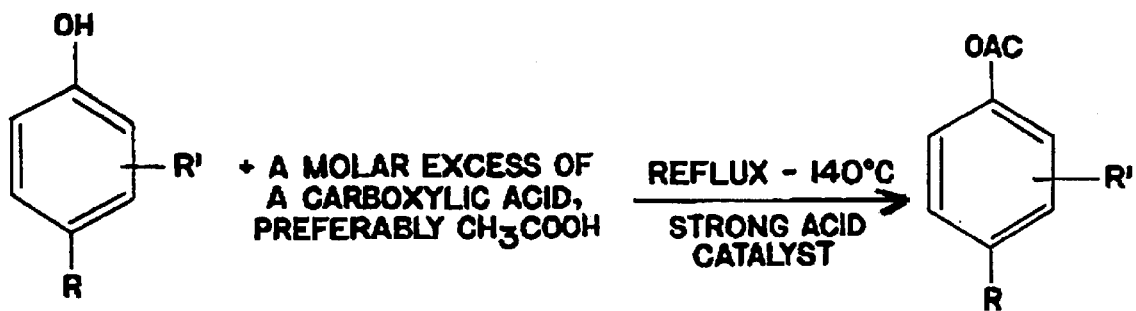
FIG. 1 is a schematic diagram illustrating one embodiment of a process for the preparation of a phenolic ester, using a carboxylic acid, for the direct esterification of an alkyl substituted phenol where the substituent(s) provide, preferably, not more than 25 alkyl carbon atoms.
Figure 2:
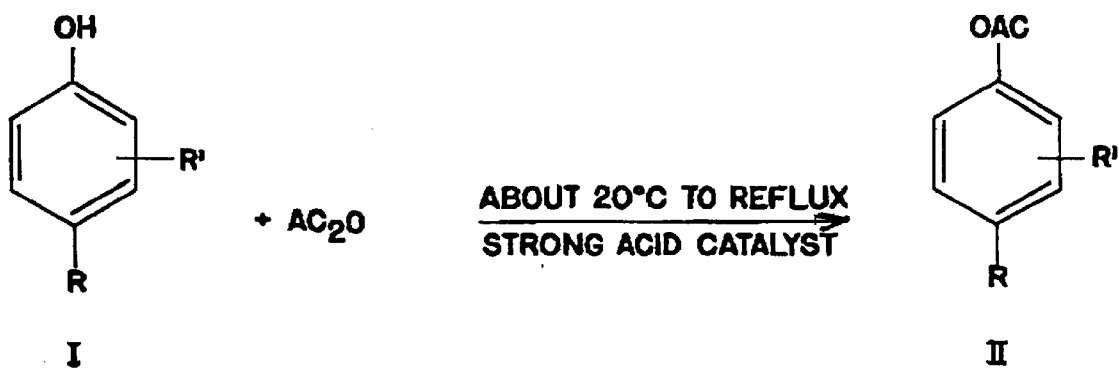
FIG. 2 is a schematic diagram depicting one embodiment of a direct esterification process using an acid anhydride to form an ester of an alkyl substituted phenol.

Generally, the processes of the invention use 4-alkylphenols as starting materials. Preferably, the starting materials are 4-isoalkylphenols, or other branched chain alkylphenols. However, the processes of the invention are operative, generally, where the alkyl substituent(s) are in other positions.

The 4-alkylphenols can be manufactured by the alkylation of phenol with olefins. Suitable, preferred olefins are: octenes; nonenes including tripropylenes; decenes; undecenes; dodecenes including triisobutylenes; tetraisopropylenes; tridecenes; and so on. Since the preferred alkyl-substituted salicylaldehyde ultimate products are those with isoalkyl or other branched chain substitution, it is preferred that this step produce a 4-isoalkyl phenol, such as, for example, most preferably, a phenol substituted in the 4 position with an isononyl or an isododecyl substituent.

However, many other branched chain alkyl-substituted phenols are useful. Among these are several compounds such as the following, where "R" in the drawings may be as described in the drawings, but is preferably, for example:

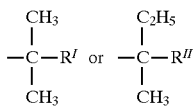

where:
$R^I$ may be isohexyl or isononyl;
$R^{II}$ may be isopentyl or isooctyl;
or where "R" in the drawings is:

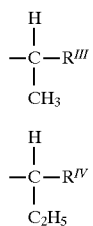

where:
$R^{III}$ may be isoheptyl; and
$R^{IV}$ may be isohexyl.

In the drawings, "R" may also be a straight chain alkyl, such as octyl, nonyl or decyl, undecyl, dodecyl, tridecyl, etc., or these alkyls could be in any of several possible branched forms or may be attached to the ring by way of any carbon making up "R".

The catalyst used for the esterifications is a strongly acid material. Generally the catalyst is a strong acid, such as concentrated sulfuric acid, methanesulfonic acid, p-toluenesulfonic acid, polyphosphoric acid, hydrochloric acid, or oxalic acid. Sulfuric acid-based catalysts such as the sulfonic acid of a phenol, p-toluenesulfonic acid, methanesulfonic acid, and trifluoromethanesulfonic acid are particularly useful. Sulfuric acid is thought to react by first sulfonating the phenolic reactant, resulting in some decrease in yield, and causing some difficulty in product isolation since the phenol sulfonate exhibits surfactant properties. It is also believed that the phenol sulfonic acid may be the true active catalyst in this case. When the catalyst is a strong sulfuric acid-based catalyst, it is generally used in the proportion of 0.001 mole of the catalytic acid per mole of phenol or phenolic derivative such as isononyl phenol. Other strongly acid materials are also useful, such as boron trifluoride, aluminum chloride, ferric chloride, and other Lewis acids. Generally, a strong acid material having a pKa of no more than 2 is preferred.

The reactions are conducted in the presence of an organic solvent that forms an azeotrope with water, to facilitate the removal of water for the purposes of driving the reaction forward and acid recovery. Toluene and xylene are preferred, but other solvents such as hexanes and heptanes would also be useful, although the reaction rates might be slower than is the case with toluene and xylene due to their lower boiling points and hence their lower reaction temperatures.

As shown and described in my copending application identified above, Ser. No. 08/635,865, filed Apr. 23, 1996, abandoned, the alkylphenols undergo a series of chemical reactions to produce 2-hydroxy-5-isoalkyl beta-methylstyrenes. The suitably alkyl-substituted styrenes, or their derivatives, are then cleaved at the propenyl moiety, to produce the corresponding alkyl substituted benzaldehydes. Cleavage is accomplished by ozonolysis. For example, when (1) 2-hydroxy-5-isoalkyl beta-methylstyrene is subjected to ozonolysis in methanol, (2) the ozonized solution is then reduced with 0.1 molar sodium thiosulfate, and (3) the product is isolated, TLC indicates that the major component present is 5-isoalkyl salicylaldehyde.

When the ozonolysis is carried out on a solution of the 2-acetoxy-5-isoalkyl beta-methylstyrene in glacial acetic acid, the acetate functionality is not affected by the ozonolysis, but the beta-methylstyrene substituent is converted to an aldehyde group, -CHO, and the acetate group can then be removed by hydrolysis. The final product is a 5-isoalkyl salicylaldehyde, again present as the major component. The isoalkyl-substituted benzaldehydes per se or their hydrolysates are substituted salicylaldehydes, which, after oximation, are useful metal extractants.

The ozonolysis can be carried out in a number of solvents including alcohols such as methanol, ethanol or isopropanol; ketones such as acetone; hydrocarbons such as toluene or heptane; carboxylic acids such as acetic acid; esters such as butyl acetate, and ethers such as dimethoxyethane or tetrahydrofuran. These reactions are generally straightforward and may be carried out readily by those skilled in the art.

The direct esterification technique of the present invention, using a carboxylic acid, is illustrated here initially through the use of acetic acid, but it should be understood that other carboxylic acids can be used as well. Another of the processes of this invention is the strong acid catalyzed esterification with acetic anhydride.

The present invention achieves reasonable conversions of alkyl substituted phenols to their carboxylates such as acetates, by direct esterification with acetic acid or other carboxylic acid, and with their anhydrides, in a short period of time. This is contrary to what one might expect based on experience and the available literature and is a surprising result.

The molar ratio of acetic acid to alkylphenol may be in the range from 1.5 to 3.5 moles of acetic acid per mole of alkylphenol. A more preferred molar ratio is in the range of 2.0–2.8 moles of acetic acid per mole of alkylphenol.

Best results for acetate formation using acetic acid appear to be achieved at a molar ratio of the acetic acid to alkylphenol, in the range of about 2.4 to 2.6 moles of acetic acid per mole of alkylphenol, in 2–4 hours. The acetic acid need not be glacial acetic acid but can be an aqueous acetic acid that may have been recovered from earlier use and that is being recycled. Generally, acid concentrations as close to 100% as is feasible for recycled material are preferred.

However, concentrations of 97% or higher produce acceptable results, and concentrations of about 90% appear to be productive. Actually, the acid concentration can be much below 90%, initially, provided that water is driven off, generally in an azeotrope with solvent, to achieve a higher concentration. Thus, the use of a dilute aqueous acid may require a longer time for the reaction, to permit water removal.

The foregoing molar ratio range is a preferred range. It is generally applicable to the $C_2$–$C_6$ carboxylic acids, however, as are the remarks about acid concentration. With longer chain carboxylic acids, some experimentation may be required to optimize the molar ratio range, operating temperature range, the preferred strong acid catalyst and amount of it to be used.

Direct esterification permits the achievement of a 65%–75% conversion of the initial alkylphenol to the ester form, preferably the acetate, in a short period of time. In order to achieve complete conversion to the acetate, it is efficient to add the acid anhydride, such as acetic anhydride, in a second step, to carry the esterification to completion. The second step of this esterification is also catalyzed by strong acids, and the esterification can be essentially completed very quickly and at a remarkably low temperature.

The advantage of following this two-step reaction procedure is that a by-product stream of recovered aqueous acetic or other carboxylic acid can be used for the majority of the initial esterification conversion, thus greatly reducing the amount of the acid, such as acetic anhydride, required for complete esterification, since the aqueous acetic acid (a condensate) can be recycled. This permits effective use of 100% of the acetic anhydride that is used in the process, a substantial economy.

Except in the Examples below, all numbers that express quantities of ingredients or reaction conditions are understood to be modified by the word "about". Throughout, all parts and percentages are by weight, and all temperatures are in degrees Celsius, unless expressly indicated to be otherwise.

PRODUCTION OF t-OCTYLPHENYL ACETATE

The literature indicates that phenols do not react to an appreciable extent in acid catalyzed esterification with carboxylic acids, nor does it appear to describe strong acid catalyzed esterification using acid anhydrides. In order to demonstrate direct esterification, many of the following examples relate to the production of t-octylphenyl acetate by direct esterification, for the most part using glacial or aqueous acetic acid. The 4-t-octylphenol was used since both it and its acetate ester are single isomers, which makes it relatively easy to do a good analysis by gas chromatography. While the isononyl and isododecylphenol acetates are of greater present commercial interest, their analyses are much more difficult because of the existence of multiple isomers.

The Examples demonstrate the effects of different reaction conditions, different reaction techniques, different reaction vehicles, and other variables. In Example 1 and the following examples, the unqualified term "acetic acid" refers to 100% (glacial) acetic acid.

EXAMPLE 1

Direct Esterification, Slow, Step-Wise Additions of Materials

Molar Ratio of Acetic Acid to 4-t-octylphenol, 2:1

A step-wise procedure of sampling, then adding more material, was used in Example 1 and in other examples, to permits development of the stoichiometry and to observe the effects of changes in the reaction conditions. For commercial scale production, single additions would be used as feasible, rather than the step-wise additions of these Examples.

A mixture of 103 g (0.5 mole) of 4-t-octylphenol, 4.75 g (5 mole %, based on the 4-t-octylphenol) of p-toluenesulfonic acid hydrate, 60 ml (1.0 mole) of acetic acid and 25 ml of toluene were combined and heated at reflux temperature (140° C.) with a packed distillation column and a Dean Stark water separator.

After 2.0 hours a sample was removed, washed two times with water, once with 5% sodium carbonate solution, and again with water. The volatiles were removed at reduced pressure and the residual was found to contain about 40% 4-t-octylphenol and 57% 4-t-octylphenyl acetate.

The 20 ml of aqueous acetic acid which had collected in the water separator were removed. The reaction temperature rose to 150° C. and dropped to 145° C. upon the charging of an additional 10 ml of toluene to the system. After 4.0 hours total reaction time, 35 ml of aqueous acetic acid had collected in the water separator. A sample of the reaction mixture, isolated as above, was found to contain about 23% t-octylphenol and 71% t-octylphenyl acetate.

An additional 15 ml of acetic acid was added to the reaction mixture, which was then refluxed for 4 more hours. The pot temperature rose to 190° C. and a total of 40 ml of aqueous acetic acid were collected in the water separator. A sample isolated as above was found to contain about 11% t-octylphenol and 72% t-octylphenyl acetate.

EXAMPLE 2

Amount of Catalyst Decreased, 5 Mole % to 1 Mole %

Molar Ratio, Acid to Phenol, 2:1

The reaction was repeated with 0.95 g (1.0 mole %) of p-toluenesulfonic acid hydrate as catalyst. After 2 hours at reflux temperature, about 140° C., a sample was isolated as above and found to contain about 48% t-octylphenol and 49% t-octylphenol acetate.

The reflux rate became slow after 3.0 hours reaction time at which point an additional 15 ml of acetic acid were added. A sample was isolated as above after 4.0 hours of reaction time and found to contain about 29% t-octylphenol and 65% t-octyl-phenyl acetate.

The reflux rate became slow again after 5.0 hours reaction time and an additional 15 ml of toluene were added to the system. After 7.0 hours of reflux time a total of 38 ml of aqueous acetic acid had been removed. The washed stripped product was found to contain about 19% t-octylphenol and 78% t-octylphenyl acetate.

Thus, a 49% yield was obtained after 2 hours of reaction time at a 2:1 mole ratio of acetic acid to the phenol, and a 78% yield after 7 hours at a mole ratio of 2.5:1.

EXAMPLE 3

Use of t-Octylphenolsulfonic Acid Catalyst

The above reaction of Example 2 was repeated with 0.9 g (1.8 mole %, based on the alkylphenol) of 98% concentration sulfuric acid, to convert the t-octylphenol to t-octylphenolsulfonic acid, to act as the true catalyst, in place of the p-toluenesulfuric acid hydrate. After 2.0 hours at reflux temperature a sample was isolated as above and found to contain about 36% t-octylphenol and 60% t-octylphenyl acetate.

After 3.0 hours reaction time an additional 15 ml of acetic acid was added to the reaction mixture. A sample was isolated as above after 4.0 hours of reaction time. It was found to contain about 21% t-octylphenol and 74% t-octylphenyl acetate.

Thus, using 1.8 mole % of sulfuric acid based on the phenol to form the phenolsulfonic acid to be the catalyst, a yield of 60% was obtained after 2 hours of reaction at a mole ratio of 2:1 of acetic acid to the phenol, and a 74% yield was obtained after 4 hours at a mole ratio of 2.5:1.

An additional 15 ml of toluene was added after 4.0 hours reaction time. After 7.0 hours at reflux temperature a total of 37 ml of aqueous acetic acid had been collected. The washed stripped product contained about 13% t-octylphenol and 81% t-octylphenyl acetate.

EXAMPLE 4

Use of 97% Acetic Acid and Then Acetic Anhydride to Drive the Reaction to Completion The reaction of Example 2 was repeated with 61.8 g of an aqueous, recycled condensate of 97% acetic acid and 3% water, using the 1.0 mole % of catalyst as in Example 2. After 2.0 hours at reflux temperature, about 140° C., a sample was isolated as before and found to contain about 49% t-octylphenol and 49% t-octylphenyl acetate.

After 3.0 hours reaction time the distillation became slow and an additional 15.5 g of 97% acetic acid were added. A sample was isolated as above after 4.0 hours reaction time and found to contain about 32% t-octylphenol and 64% t-octylphenyl acetate. The rate of distillation had become slow again, at a pot temperature of 153° C., and an additional 15 ml of toluene was added to the reaction.

A sample was isolated as above after 6.0 hours total reaction time and found to contain about 24% t-octylphenol and 73% t-octylphenyl acetate. After 8.0 hours total reaction time a total of 40 ml of aqueous acetic acid was collected and the product contained about 20% t-octylphenol and 76% t-octylphenyl acetate.

The reaction was then driven to completion by the addition of 11.2 g of acetic anhydride at 73° C., held at about 80° C. for 30 minutes, then allowed to cool to room temperature. The final product contained about 0.4% t-octylphenol and 95% t-octylphenyl acetate.

Subsequent observations indicate that the final step, involving the use of acetic anhydride, can be conducted at temperatures higher or lower than the 80° C. used in Example 4.

EXAMPLE 5

Comparative Example

Attempted Direct Esterification—No Catalyst

The above Example 4 reaction was repeated with no strong acid added as catalyst. After 2.0 hours at reflux, no t-octylphenyl acetate was detected.

EXAMPLE 6

Xylene Vehicle

The reaction of Example 1 was repeated, but it was run with 25 ml of xylenes (in place of the toluene used in Example 1) in the mixture of 103 g of t-octylphenol, 4.75 g of p-toluenesulfonic acid hydrate, and 60 ml of acetic acid (AA). A sample was isolated as above after 2.0 hours reaction time at about 145° C. and found to contain 40% t-octylphenol and 60% t-octylphenyl acetate.

After 4.0 hours at reflux temperature the product contained 24% t-octylphenol and 70% t-octylphenyl acetate, and an additional 25 ml of acetic acid were added.

An additional 25 of xylenes were added after 4.0 hours and 45 minutes total reaction time. A washed stripped sample contained 11.5% t-octylphenol and 76% t-octylphenyl acetate.

EXAMPLE 7

Direct Esterification—Effect of Reaction Time and Large Molar Excess of Acid

AA:Phenol Molar Ratio, 10:1

The primary purpose of this demonstration of the invention was to determine how far toward completion the reaction could be driven, given sufficient time.

A mixture of 103 g(0.5 mole) of 4-t-octylphenol, 4.75 g(5 mole %) of p-toluenesulfonic acid hydrate, 300 g(5.0 moles) of acetic acid (AA) and 30 ml of toluene was heated at reflux temperature with a packed distillation column and a Dean Stark water separator. A sample was isolated as above after 2.0 hours at reflux temperature and found to contain about 61% t-octylphenol and 37% t-octylphenyl acetate.

An additional 25 ml of toluene were added to the reaction mixture after 2.0 hours at reflux temperature. A sample was isolated as above after 7.0 hours at reflux temperature and found to contain about 34% t-octylphenol and 69% t-octylphenyl acetate.

After 15.0 hours at reflux temperature the product contained about 15% t-octylphenol and 83% t-octylphenyl acetate.

After 23.0 hours at reflux temperature it contained about 9% t-octylphenol and 92% t-octylphenyl acetate.

After 31.0 hours under reflux conditions it contained about 5% t-octylphenol and 96% t-octylphenyl acetate. Examination by GC/IR found no unsubstituted phenol or phenyl acetate.

EXAMPLE 8

Slow Addition of Acetic Acid

AA:Phenol Molar Ratio, 2:1

A mixture of 103 g of t-octylphenol, 0.95 g of p-toluenesulfonic acid hydrate (1 mole %) and 25 ml of toluene was heated to 160° C.–165° C. with a packed distillation column and Dean Stark water collector. A total of 60 ml of acetic acid was pumped slowly into the bottom of the reaction mixture over about a three hour period of time. The temperature remained at 160° C.–165° C. during the first half of the addition, then gradually dropped to 105° C. during the remainder of the acetic acid addition. A sample was isolated after 3.0 hours total reaction time and found to contain about 45% t-octylphenol and 50% t-octylphenyl acetate.

After 4.0 hours total reaction time the product contained about 37% t-octylphenol and 59% t-octylphenyl acetate with 28% t-octylphenol and 66% t-octylphenyl acetate after 6.0 hours total reaction time. After 7.0 hours total reaction time the product contained 24% t-octylphenol and 70% t-octylphenyl acetate.

EXAMPLE 9

Methanesulfonic Acid Catalyst and 97% Acetic Acid

AA:Phenol Molar Ratio, 2:1

A mixture consisting of 103 g(0.5 mole) of 4-t-octylphenol, 61.8 g (1.0 mole) of 97% acetic acid with 3% water, 25 ml of toluene and 0.24 g (0.0025 mole=0.5 mole %) of methanesulfonic acid was heated at reflux temperature. The vapors were fractionated with a distillation column which had about nine theoretical plates. The resultant distillate was continuously collected in a Dean Stark water separator.

After four hours at reflux, 28 ml of distillate which contained about 72% acetic acid, 8% toluene and 20% water had been collected. An additional 15.5 g(0.25 moles) of 97% acetic acid was then added, and the reaction was continued at reflux temperature. After a total of 8.0 hours at reflux temperature, a total of 39 ml of azeotropic distillate had been collected. A sample was isolated from the reaction mixture and found to contain about 26% t-octylphenol and 71% t-octylphenyl acetate.

EXAMPLES 10A AND B

10A. Oxalic Acid Catalyst Using 97% Acetic Acid

AA:Phenol Molar Ratio, 2:1

A mixture of 103 g of 4-t-octylphenol, 61.8 g of 97% acetic acid, 25 ml of toluene and 0.45 g(1 mole %) oxalic acid was heated at reflux temperature for 8.0 hours with the distillation column and water separator described in Example 9. A sample of the reaction mixture was isolated and found to contain about 97% t-octylphenol and 2% t-octylphenyl acetate.

10B. Oxalic Acid Catalyst Using (Glacial) Acetic Acid

AA:Phenol Molar Ratio, 2:1

A mixture consisting of 103 g (0.5 mole) of 4-t-octylphenol, 60.0 g of acetic acid, 1.8 g of water, 0.45 g (1 mole %) of oxalic acid and 25 ml of toluene was heated at reflux temperature for 8 hours with a packed distillation column and a Dean Stark water separator as a collector. During this period of time 7.5 ml of distillate were collected. A sample was found to contain about 97% 4-t-octylphenol and 1.6% 4-t-octylphenyl acetate.

EXAMPLES 11A and B

11A. Strong Acid Catalyst, Moles of Acetic Acid Increased Over Example 10 And No Co-Solvent AA:Phenol Molar Ratio, 2.5:1

A mixture of 103 g(0.5 mole) of 4-t-octylphenol, 75 g(1.25 mole) of acetic acid and 0.95 g(1 mole %) of p-toluenesulfonic acid hydrate was heated at reflux temperature with the distillation column described in Example 9. Aqueous acetic acid was periodically collected from the Dean Stark water separator. Samples were isolated from the reaction product after 5.0 and 8.0 hours at reflux temperature and found to contain about 51% t-octylphenol and 47% t-octylphenyl acetate, and 37% t-octylphenol, 60% t-octylphenyl acetate, respectively.

11B. Strong Acid Catalyst, Moles of Acetic Acid Increased Over Example 10 And No Co-Solvent AA:Phenol Molar Ratio, 2.5:1

A mixture consisting of 103 g (0.5 mole) of 4-t-octylphenol, 75 g (1.25 moles) of acetic acid and 0.95 g (1 mole %) of p-toluenesulfonic acid hydrate was maintained at reflux temperature for 8 hours with a packed distillation column and a Dean Start water separator. Over a 7 hour period of time 35 ml of distillate was collective incrementally. After 5 hours at reflux temperature a sample was found to contain about 47% 4-t-octylphenyl acetate and 51% 4-t-octylphenol with 60% and 37% of each respectively after 8 hours.

Comments

As demonstrated in these Examples, an organic co-solvent is desirable but not essential.

EXAMPLE 12

Larger Scale Repetition of Example 4

Example 4 was repeated but on twice the scale described in Example 4. After the esterification had been driven to completion with acetic anhydride, the toluene and by-product acetic acid were removed at reduced pressure. This distillate and the azeotropic distillate consisting of water, acetic acid and toluene were combined to give a mixture consisting of about 118.2 g of acetic acid, 69.6 g of toluene and 18.1 g of water. This mixture was fractionally distilled with a distillation column which had about 9 theoretical plates. A total of about 20 g of distillate was collected which contained about 25% acetic acid, 0.25–0.5% toluene, and the balance water. The distillation residue was eminently suitable for recycling to the original esterification reaction after the addition of the requisite amount of additional acetic acid, i.e., about 45 g.

THE EFFICACY OF DIFFERENT ACID CATALYSTS

Several different strong acids were used as catalysts for the esterification. Generally, the amount of a particular strong acid material is readily optimized, and will fall in the range from about 0.1 mole % to about 10 mole %, based on the phenol. For commercial production, generally the least amount of catalyst is used that will produce the desired result.

The reactions using the different strong acid catalysts, and their results, are described in Examples 13–24 below, as is the use of the ester product to produce an important intermediate used in the production of a copper extractant.

EXAMPLES 13–24

A first step in the formation of the LIX®84 ketoxime is the esterification of nonylphenol (NP) with acetic anhydride to produce p-nonylphenylacetate (NPA). This esterification can be readily effected with a slight excess of acetic anhydride. The reaction is essentially complete in two hours at 140° C. and atmospheric pressure. A comparable degree of esterification can be achieved in 24 hours at 110° C.

However, due to concern about the corrosion of the stainless steel heat exchanger on the reactor due to the byproduct acetic acid at 140° C., an alternate strong acid catalyzed esterification procedure was developed. With 0.001 mole of sulfuric, p-toluenesulfonic or methanesulfonic acid per mole of nonylphenol, the esterification is complete in one hour at 70° C. to 80° C.

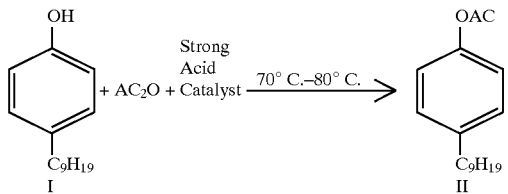

The product from any of these esterification procedures will typically contain <1% residual p-nonylphenol, 1% to 3% o-nonylphenol and <2% dinonylphenol. Such crude ester is well suited for the subsequent rearrangement without further purification.

Methanesulfonic acid is the catalyst of choice due to a combination of its efficacy, low corrosivity, high water solubility and thus easy removal from the product, and the reduced likelihood of its forming surface active byproducts which would have a negative effect on product performance. Other acids including 85% phosphoric acid, oxalic acid, and trichloroacetic acid were evaluated and found to be less effective than the sulfuric acid based products. The results of this investigation are summarized in Table 1, below.

REARRANGEMENT

The second step in the process is a Fries Rearrangement of 4-nonylphenyl-acetate (II) to 2-hydroxy-5-nonylacetophenone (HNA, III). In its simplest form the reaction is:

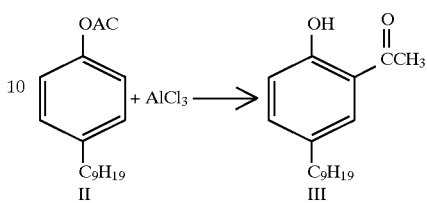

GENERAL CONSIDERATIONS

While several of the foregoing Examples of the invention are focused on the production of t-octylphenyl acetate to demonstrate the invention, the reaction itself is of much more general utility. It is useful for esterifying phenol as well as substituted phenols.

An alkyl substituent on the phenol, for example, can be any single alkyl up to 25 carbons in chain length. The substituent need not be a straight line chain, but can be branched, as needed for the production of particular compounds. The acetates of isononyl- and of isododecyl-substituted phenols are of some commercial interest and are

TABLE 1

ACID CATALYZED ESTERIFICATION

| Ex. | Acid, Amt./mole of nonylphenol | Exotherm °C. | Completion of Exotherm (Time)1 | Total Reaction Time2 | NPA(%)3 | o-NP(%)4 | p-NP(%)4 |
|---|---|---|---|---|---|---|---|
| 13 | H$_2$SO$_4$ (1 mg)/mole nonyl phenol | 73° | (2 min) | 3 hr | 58 | 5.0 | 35 |
| 14 | H$_2$SO$_4$ 10 mg/mole | 93° | (2 min) | 30 min | 96 | 3.5 | 3 |
| 15 | H$_2$SO$_4$ 10 mg/mole | RT → 64° | (2 min) | 3 hr (20 min) | 96 | 2.2 2.5 | .25 0.4 |
| 16 | Polyphosphoric (10 mg)/mole | 60° | | 2.5 hr | 69.2 | 4.5 | 21.3 |
| 17 | AlCl$_3$ | 75° | | 2 hr | 75 | 2.4 | 19.4 |
| 18 | Methanesulfonic (1 m mole)/mole | 85° | (4 min) | 1 hr | 95.5 | 2.5 | .5 |
| 19 | Methanesulfonic (10 m mole)/mole | 95° | (1 min) | 5 min | 96.0 | 1.3 | — |
| 20 | p-Toluenesulfonic (1 m mole)/mole | 95° | (4 min) | 30 min | 94.8 | 1.3 | — |
| 21 | Methanesulfonic (1 m mole) mole nonylphenol-30 min addition time | 80° | | 45 min | 95.7 | 1.8 | — |
| 22 | Pilot Plant | 82° | | 30 min | 95.6 | 1.45 | .83 |

ACID CATALYZED ESTERIFICATION

| Ex. | Acid, Amt./mole of nonylphenol | Exotherm °C. | Total Reaction Time2 | NPA(%)3 | o-NP(%)4 | p-NP(%)4 |
|---|---|---|---|---|---|---|
| 23 | Oxalic (2 m mole)/mole | 60° | 12 hr | 49.0 | 5.5 | 43.6 |
| 24 | CCl$_3$CO$_2$H (2 m mole)/mole | 55° | 12 hr | 50.3 | 5.0 | 37.3 |

1"time" is time required for exotherm completion.
2"time" is reaction time.
3NPA = nonylpenol acetate
4NP = nonylphenol readily produced by the esterification techniques of this invention. The reaction is not confined to phenols having these alkyl substituents, however.

Among the many other alkyl substituents on the phenols, that are expected to be useful, are pentyl and isopentyl; hexyl and isohexyl; heptyl, isoheptyl, and t-heptyl; octyl, isooctyl, and 2-ethylhexyl, as well as t-octyl; nonyl, isononyl, and t-nonyl; decyl, isodecyl, and t-decyl; undecane, iso-undecane, and t-undecane; dodecane and t-dodecane, as well as isododecane; and similarly, the same is true for the $C_{14}$–$C_{25}$ alkanes.

Direct esterification is also feasible where there is more than a single alkyl substituent on the phenol. Generally, however, for reasons of economy, the phenol used in the reaction will have only a single alkyl substituent.

The alkyl substituent or substituents may also be derivatized. Generally, however, non-derivatized alkyl substituents are preferred for economy and more ready availability.

The present application has emphasized the production of acetic acid esters of alkyl-substituted phenols. The acetic acid forms acetates that are inexpensive and that are easily removed and replaced, which are very useful properties in an intermediate. Thus, there appears to be no obstacle to the use of direct esterification with other carboxylic acids such as, for example, propionic, butyric, isobutyric, and so on, although for the production of the intermediates discussed above there is no reason to use these more expensive and less easily reacted and handled acids.

Generally, strong acid catalysts are preferred for direct esterification. Thus, the aryl sulfonic acids tend to be catalysts of choice, although other strong acids, particularly the mineral acids, are operative. The strong acids that are preferred are those that have a dissociation constant, pKa, of not above 2. Generally, the more strongly dissociated an acid is, the lower will be its pKa.

In a preferred embodiment of the invention, it is a method of producing an ester of an alkyl phenol and acetic acid comprising reacting the alkylphenol with a molar excess of acetic acid at reflux temperature, in the presence of a strong acid catalyst, and in an aqueous sytem that comprises a hydrocarbon solvent that forms an azeotrope with water. The alkyl substituent of the alkylphenol should provide not more than 25 alkyl carbons per molecule of the alkylphenol. Preferably, the alkyl substituent is branched for improved solubility in hydrocarbon solvents. The molar ratio of acetic acid to the alkylphenol, during this reaction, may be in the range from 1.5 to 3.5 moles of acetic acid per mole of alkylphenol. A preferred molar ratio is 2.0 to 2.8 moles of acetic acid per mole of alkylphenol, and a most preferred molar ratio is 2.4 to 2.6 moles of acetic acid per mole of alkylphenol.

Optionally, after the initial esterification reaction has gone forward to the point where the reaction product comprises at least 40% but preferably at least 50% by weight of an acetate ester of the alkylphenol, the reaction is moved further toward completion by adding acetic anhydride to the reaction product and heating at an elevated temperature as necessary, and for a sufficient period of time, to permit substantial completion of ester formation.

The preferred alkylphenols, with which the esterification process of the invention may be practiced, are 4-isononylphenol and 4-isododecylphenol. However, as has been demonstrated in the Examples, the esterification process works well with t-octylphenol, as it does also with the preferred substrate alkylphenols having alkyl substituents with 6–18 carbons in a single alkyl substituent per molecule.

Branched chain alkyl substituents are preferred but the process is equally operative with straight chain alkyl-substituted phenols.

Optionally, for use in the production of metal extractants for which this invention was developed, the alkylphenol may have a functional substituent at the 2 position, and the alkyl substituent will then be in the 4 position, on the phenyl ring.

While the foregoing description has been applied to direct esterification using acetic acid, the invention also provides an improved process for using acetic anhydride for direct esterification. The improvement accrues in part from the strong acid catalyzed esterification with acetic anhydride.

The use of a distillation column preferably having at least nine theoretical plates, used to collect vapors above the refluxing reaction for recycling purposes, and for recovery of the acetic acid, permits a more economical process than previously available.

A hydrocarbon solvent is useful, particularly if it forms an azeotrope that is readily condensed, for recovery of the condensate.

The abbreviation "TLC" stands for thin layer chromatography.

While the invention has been described in connection with specific embodiments thereof, it should be understood that the invention is not confined to those specific embodiments that have been exemplified, but should be accorded the scope of the appended claims.

What is claimed is:

1. A method for producing an ester of a phenol and a carboxylic acid comprising:

reacting a phenol with a carboxylic acid anhydride in the presence of a strong acid catalyst, wherein said strong acid catalyst is selected from the group consisting of a sulfonic acid-based catalyst, a sulfuric acid-based catalyst, and mixtures thereof, and wherein the molar amount of said carboxylic acid anhydride is in slight excess to the molar amount of said phenol of at least 1.01 moles of said acid anhydride to 1.00 mole of said phenol.

2. The method of claim 1, wherein said strong acid catalyst is selected from the group consisting of sulfuric acid, paratoluenesulfonic acid, methanesulfonic acid, trifluoromethanesulfonic acid, polyphosphoric acid, aluminum trichloride, ferric chloride, zinc chloride, hydrogen chloride, boron trichloride, oxalic acid, trichloroacetic acid, a phenol sulfonic acid, and the like.

3. The method of claim 1, wherein said reaction is carried out at a temperature of at least 70° C.

4. The method of claim 1, wherein said catalyst comprises a sulfonic acid of an alkylphenol.

5. The method of claim 1, wherein said molar excess in the range of 1.01 to 2.00.

6. The method of claim 1, wherein said phenol comprises an alkylphenol wherein the alkyl substitution on the phenol contains at most 25 carbons.

7. The method of claim 6, wherein said phenol comprises at least one branched chain alkyl substituent.

8. The method of claim 7, wherein said alkylphenol comprises nonylphenol or dodecylphenol.

9. The method of claim 6, wherein said alkylphenol comprises an isoalkylphenol.

10. The method of claim 6, wherein said alkylphenol has a functional substituent of the 2 position and wherein one alkyl substituent is at the 4 position.

11. The method of claim 10, wherein said 4-alkyl substituent comprises isononyl or isododecyl.

12. A method for producing an ester of a phenol and a carboxylic acid comprising reacting a phenol with a molar excess of a carboxylic acid to said phenol in the presence of a strong acid catalyst.

13. The method of claim 12, wherein the molar ratio of said carboxylic acid to said phenol is in the range of 1.5 to 3.5.

14. The method of claim 12 comprising reacting a phenol with a molar excess of a carboxylic acid to said phenol in the range of 1.5–3.5, in the presence of a strong acid catalyst, at reflux temperature, condensing reflux vapors and recovering at least a part of the carboxylic acid as condensate, for optional recycling in said method, and optionally adding to the reaction mixture an anhydride of said carboxylic acid and reacting further, to drive the reaction further toward completion.

15. The method of claim 13, wherein said strong acid catalyst is selected from the group consisting of sulfuric acid, paratoluenesulfonic acid, methanesulfonic acid, trifluoromethanesulfonic acid, polyphosphoric acid, aluminum trichloride, ferric chloride, zinc chloride, hydrogen chloride, boron trichloride, oxalic acid, trichloroacetic acid, a phenol sulfonic acid, and the like.

16. The method of claim 13, wherein said phenol is an alkylphenol and has a functional substituent at the 2 position, and wherein said alkyl substituent is in the 4 position on the phenyl ring.

17. The method of claim 14, wherein said strong acid catalyst is selected from the group consisting of sulfuric acid, paratoluenesulfonic acid, methanesulfonic acid, trifluoromethanesulfonic acid, polyphosphoric acid, aluminum trichloride, ferric chloride, zinc chloride, hydrogen chloride, boron trichloride, oxalic acid, trichloroacetic acid, a phenol sulfonic acid, and the like.

18. The method of claim 17, wherein said phenol is an alkylphenol and has a functional substituent at the 2 position, and wherein said alkyl substituent is in the 4 position on the phenyl ring.

19. A method for producing an ester of an alkylphenol and a carboxylic acid comprising reacting said alkylphenol with a molar excess of a carboxylic acid in the presence of a strong acid catalyst, at reflux temperature, in the presence of an organic solvent that forms an azeotrope with water, condensing vapors of said azeotrope and recovering at least a part of the condensate including at least a part of said carboxylic acid, for optional recycling in said method, and optionally adding to the reaction mixture an anhydride of said carboxylic acid and reacting further, to drive the reaction further toward completion.

20. The method of claim 19, wherein said alkylphenol comprises an isoalkyl-substituted phenol having not more than 25 alkyl carbons per molecule in said alkyl substituent.

21. The method of claim 20, wherein said carboxylic acid comprises at least in part aqueous carboxylic acid recovered from said condensate.

22. The method of claim 21, wherein said alkyl substituent comprises isononyl or isododecyl.

23. The method of claim 19, wherein said strong acid catalyst has a pKa of not more than 2.

24. The method of claim 19, wherein said strong acid catalyst is selected from the group consisting of a sulfonic acid-based catalyst, and a sulfuric acid-based catalyst, and mixtures thereof.

25. The method of claim 6, wherein said strong acid catalyst comprises methanesulfonic acid.

26. The method of claim 19, wherein said carboxylic acid comprises acetic acid.

27. The method of claim 19, wherein said molar ratio of said carboxylic said to said alkylphenol is in the range of 1.5–3.5.

28. The method of claim 27, wherein said molar ratio is in the range of 2.0–2.8.

29. The method of claim 21, wherein said alkylphenol has a substituent at the 2 position, wherein its phenolic hydroxy group is at the 1 position, and wherein said alkyl substituent comprises a branched chain alkyl group of 6–18 carbons, in the 4 position on said phenolic molecule.

30. A method for producing an ester of an alkylphenol having not more than 25 alkyl carbons per molecule and a carboxylic acid comprising reacting said alkylphenol with a molar excess of carboxylic acid in the range of 1.5 to 3.0 moles of said carboxylic acid to said alkylphenol, at reflux temperature and in the presence of a strong acid catalyst, and further in the presence of an organic solvent that forms an azeotrope with water, wherein said strong acid catalyst is selected from the group consisting of a sulfonic acid-based catalyst, a sulfuric acid-based catalyst, and mixtures thereof, condensing vapors of said azeotrope and recovering at least a part of the condensate including at least a part of said carboxylic acid, for optional recycling in said method, and optionally adding to the reaction mixture an anhydride of a carboxylic acid and reacting further, to drive the reaction further toward completion.

31. The method of claim 30, wherein at least a part of said alkyl substituent comprises a branched chain alkyl, and wherein said carboxylic acid comprises acetic acid, and further wherein said molar ratio is in the range of 2.0–2.8 moles of acetic acid per mole of alkylphenol.

32. The method of claim 31, wherein said strong acid catalyst has a pKa of not more than 2, and wherein said organic solvent comprises a hydrocarbon.

33. A method of producing an ester of an alkylphenol and a carboxylic acid having up to 6 carbons per molecule comprising reacting said alkylphenol with a molar excess of said carboxylic acid in the presence of a strong acid catalyst, at a reflux temperature, wherein said alkyl substituent provides not more than 18 alkyl carbons per molecule of said alkylphenol, said molar ratio of said carboxylic acid to said alkylphenol is in the range from about 1.5 to about 3.5, and said strong acid catalyst has a dissociation constant pKa of not more than 2.0, and optionally, adding to the reaction mixture the anhydride of said carboxylic acid and reacting further, to drive the reaction further toward completion.

34. The method of claim 33, wherein said reaction is carried out in the presence of a liquid vehicle that forms an azeotrope with water.

35. The method of claim 34 including generating said azeotrope at said reflux temperature and condensing the vapors for possible recycling to said reaction of its carboxylic acid content.

36. The method of claim 35, wherein said liquid vehicle comprises a hydrocarbon.

37. The method of claim 35, wherein said alkyl substituent comprises a branched chain alkyl group.

38. The method of claim 37, wherein said alkyl substituent comprises isononyl.

39. The method of claim 37, wherein said alkyl substituent comprises isododecyl.

40. The method of claim 35, wherein said molar ratio is in the range from about 1.5 to about 3.5.

41. The method of claim 40, wherein said molar ratio is in the range from about 2.0 to about 2.8.

42. The method of claim 35, wherein said strong acid catalyst comprises p-toluenesulfonic acid.

43. The method of claim 35, wherein said strong acid catalyst comprises sulfuric acid.

44. The method of claim 35, wherein said strong acid comprises methanesulfonic acid.

45. The method of claim 35, wherein said catalyst is a phenol sulfuric acid.

46. The method of claim 33, wherein said alkylphenol has a substituent at the 1 position, wherein its phenolic hydroxy group is at the 2 position, and wherein said alkyl substituent comprises a branched chain alkyl group of 6–18 carbons in the 4 position on said phenolic molecule.

47. The method of claim 35, wherein said aqueous system comprises a liquid vehicle that forms a azeotrope with water, said strong acid catalyst is selected from the group consisting of a sulfonic acid and a sulfuric acid, and wherein said molar ratio is in the range from 2.0 to 2.8.

48. The method of claim 47, wherein said carboxylic acid comprises acetic acid, and wherein said acid anhydride, if used, comprises acetic anhydride.

49. The method of claim 48, wherein said strong acid catalyst comprises methanesulfonic acid.

50. A method of producing an ester of an isoalkylphenol and a carboxylic acid having up to 6 carbons per molecule, comprising reacting said isoalkylphenol with a molar excess of a carboxylic acid in the presence of a strong acid catalyst, at a reflux temperature, in an aqueous system that comprises a liquid vehicle that is inert with respect to said reactants, and that comprises an organic solvent that forms an azeotrope with water, wherein said isoalkyl substitution provides not more than 18 isoalkyl carbons per molecule of said isoalkylphenol and comprises a branched chain alkyl group, said molar ratio of said carboxylic acid to said alkylphenol is in the range from about 1.5 to about 3.5, and said strong acid catalyst has a dissociation constant pKa of not more than 2.0, and optionally, adding to the reaction mixture the anhydride of said carboxylic acid and reacting further, to drive the reaction further towards completion.

51. The method of claim 50 further comprising the step of condensing vapors generated at said reflux temperature and recovering at least a part of said condensate containing at least a part of the said carboxylic acid, for possible recycling in said method.

52. The method of claim 51, wherein said molar ratio is in the range from about 2.0 to about 2.8, and wherein said isoalkylphenol has a substitutent at the 2 position, wherein its phenolic hydroxy group is at the 1 position, and said alkyl substitutent comprises a branched chain alkyl group of 6–18 carbons and is at the 4 position of said phenolic molecule.

53. The process of claim 52, wherein said carboxylic acid comprises acetic acid, and said acid anhydride, if used, comprises acetic anhydride.

54. A method of producing an ester of an alkylphenol and acetic acid, comprising reacting said alkylphenol with a molar excess of acetic acid in the presence of a strongly acid catalyst, at a reflux temperature, and in an aqueous system that comprises a hydrocarbon solvent that forms an azeotrope with water, and condensing vapors of said azeotrope and recovering at least a part of the condensate including at least a part of said carboxylic acid, for optional recycling in said method, wherein said alkyl substituent provides 6–18 alkyl carbons per molecule of said alkylphenol and wherein said alkyl substituent comprises branched chain alkyl, said molar ratio of said acetic acid to said alkylphenol is in the range from about 2.0 to about 2.8, and said strongly acid catalyst has a dissociation content pKa of not more than 2.0, and optionally, after said reaction has gone forward to the point where the reaction product comprises at least 40% by weight of an acetate ester of said alkylphenol, reacting said reaction product further with acetic anhydride to drive said reaction further toward completion of said ester formation.

55. The process of claim 54, wherein said alkylphenol has a substituent at the 2 position, its phenolic hydroxy group at the 1 position, and said alkyl substituent comprises a branched chain alkyl group of at least 8 carbons in the 4 position on said phenolic molecule.

56. The method of claim 55, wherein said alkyl substituent comprises isononyl.

57. The method of claim 55, wherein said alkyl substituent comprises isododecyl.

58. The method of claim 54 comprising fractionating said azeotrope reflux in a distillation column having at least 9 theoretical plates, collecting at least some of the vapor in a water separator, and returning a hydrocarbon portion of the distillate to the reaction.

59. A method of producing an ester of a phenol and acetic acid, comprising reacting a phenol with acetic anhydride in the presence of a strong acid catalyst at an elevated temperature, and in the presence of a volatile organic solvent that forms an azeotrope with water, condensing vapors of said azeotrope and recovering at least a part of the condensate including at least a part of said acid, for optional recycling in said method.

60. The method of claim 59, wherein said reaction is conducted in a aqueous system comprising a volatile hydrocarbon solvent, and said reaction is carried out at an elevated reflux temperature above about 70° C.

61. The method of claim 61, wherein said phenol comprises an alkylphenol having not more than 25 alkyl carbons per molecule.

62. The method of claim 61, wherein said alkyl substituent comprises an isononyl group.

63. The method of claim 61, wherein said alkyl substituent comprises an isododecyl group.

* * * * *